United States Patent [19]

Kiyoura et al.

[11] Patent Number: 5,032,564
[45] Date of Patent: Jul. 16, 1991

[54] PROCESS FOR PRODUCING CATALYST PRECURSOR AND CORRESPONDING CATALYST

[75] Inventors: Tadamitsu Kiyoura; Jimbo, Takashi; Yasuo Kogure; Kazuo Kanaya, all of Kanagawa, Japan

[73] Assignee: Mitsui Toatsu Chemicals, Inc., Tokyo, Japan

[21] Appl. No.: 482,492

[22] Filed: Feb. 21, 1990

[30] Foreign Application Priority Data

Feb. 23, 1989 [JP] Japan .................................. 1-41493

[51] Int. Cl.⁵ .............................................. B01J 27/198
[52] U.S. Cl. ................................................... 502/209
[58] Field of Search ........................................ 502/209

[56] References Cited

U.S. PATENT DOCUMENTS

| 4,132,670 | 1/1979 | Katsumoto et al. | 423/305 X |
| 4,283,288 | 8/1981 | Udovich et al. | 502/209 |
| 4,365,069 | 12/1982 | Bremen et al. | 549/260 |
| 4,434,244 | 2/1984 | Kuhlmann et al. | 502/209 |

FOREIGN PATENT DOCUMENTS

| 0036623 | 3/1981 | European Pat. Off. . |
| 0106927 | 10/1982 | European Pat. Off. . |
| 0151912 | 12/1984 | European Pat. Off. . |

*Primary Examiner*—W. J. Shine
*Attorney, Agent, or Firm*—Burns, Doane, Swecker & Mathis

[57] ABSTRACT

A cayalyst precursor is produced by reacting $V_2O_4$ with phosphoric acid in an organic solvent in the presence of a polyol. The catalyst precursor is calcined to obtain a catalyst having a high density, highly attrition-resistance and a large specific surface area and requiring only a low temperature for the oxidation of butane.

5 Claims, No Drawings

PROCESS FOR PRODUCING CATALYST PRECURSOR AND CORRESPONDING CATALYST

BACKGROUND OF THE INVENTION

1. Field of the Invention

This invention relates to a process for producing a catalyst precursor and a corresponding catalyst for manufacturing maleic anhydride by oxidizing butane.

2. Description of the Related Art

Heretofore, compounds comprising vanadium and phosphorus have been used as catalysts for processes for producing maleic anhydride by oxidizing a saturated hydrocarbon of 4 carbon atoms, usually, n-butane, with an oxygen-containing gas. It has been known that the compound comprising vanadium and phosphorus effective as the catalyst is a crystalline compound having the formula $(VO)_2P_2O_7$. In order to obtain a compound having the formula $(VO)_2P_2O_7$ as an effective component of the catalyst, usually, $V_2O_5$ is reduced to $V_2O_4$ by the conventional method and the $V_2O_4$ is reacted with phosphoric acid to form $(VO)_2H_4P_2O_9$ followed by thermal decomposition. The catalyst precursor, $(VO)_2H_4P_2O_9$, can be produced usually by reacting $V_2O_5$ with a reducing agent and phosphoric acid in an organic solvent, particularly, in an alcohol such as isobutyl alcohol. The reaction results in precipitation of the desired product, $(VO)_2H_4P_2O_9$. This precipitation is advantageous for isolating and collecting the effective catalyst component.

U S Pat. No. 4,132,670 discloses that $V_2O_5$ is reduced to $V_2O_4$ in an alcohol in the presence of a dihydric alcohol and the resulting $V_2O_4$ is reacted with phosphoric acid to form the catalyst precursor, $(VO)_2H_4P_2O_9$, so as to obtain a catalyst having the formula $(VO)_2P_2O_7$ and a large specific surface area. According to its example, glycerine is added to amyl alcohol to reduce $V_2O_5$ to $V_2O_4$, which is then reacted with phosphoric acid to produce the catalyst precursor. However, nothing is mentioned about its function and effect where the polyhydric alcohol is used.

U.S. Pat. No. 4,396,535 discloses a process for reducing $\alpha$-$VOPO_4$ to $(VO)_2P_2O_7$ in an organic medium, but nothing is mentioned about its function and effect where reduction is carried out by using a polyhydric alcohol as an organic medium.

EP 98,039 discloses that ethylene glycol is used as an organic medium upon reducing $V_2O_5$, but neither concrete working examples for its effects are disclosed.

U.S. Pat. Nos. 4,365,069 and 4,448,893 disclose methods for reducing a pentavalent vanadium in the presence of an alcohol and a glycol and reacting with phosphoric acid, but any effect and concrete working examples concerning using the glycol are not disclosed.

However, the catalyst produced by thermally decomposing a precursor comprising $(VO)_2H_4P_2O_9$ has a density of 1 g/ml or less and is poor in mechanical strength. In particular, when the catalyst is used as a catalyst in a fluidized bed, its attrition-resistance is so poor that it can not withstand actual industrial operations. In conventional processes for producing catalysts for fluidized beds, a slurry prepared by suspending the catalyst precursor in water is spray-dried, and the resulting spray-dried product is thermally decomposed. However, the thus-prepared catalyst has a low density and poor attrition-resistance.

In order to solve the above problems, it has been proposed to finely pulverize the precipitated catalyst precursor to a size of 1 $\mu$m or less by using a mechanical means such as a ball mill and the like. Subsequently, the pulverized precursor is suspended in water to form a slurry, which is then spray-dried and calcined (see Japanese Patent Application Laid-Open No. 55,350/84). This procedure, however, is complicated, and the attrition-resistance of the resulting catalyst is still insufficient. The surface area of the resulting catalyst is small, and when the catalyst is used for the oxidation of butane to produce maleic anhydride, the oxidation must be conducted at a temperature as high as 430° to 450° C. As a result, the selectivity in forming maleic anhydride is low.

OBJECTS AND SUMMARY OF THE INVENTION

An object of the present invention is to provide a process for producing a catalyst having a high density, high attrition-resistance, a large specific surface area and requiring only a low reaction temperature for the oxidation of butane.

Another object of the present invention is to provide a process for producing a catalyst precursor to give the same catalyst.

A catalyst precursor for oxidizing butane to maleic anhydride is obtained by reacting $V_2O_4$ with phosphoric acid in an organic solvent in the presence of a polyol.

DESCRIPTION OF THE PREFERRED EMBODIMENTS

The catalyst precursor obtained according to the process of the present invention can be separated from the organic solvent and then suspended in water to form an aqueous slurry, which is spray-dried and calcined to produce a catalyst comprising $(VO)_2P_2O_7$.

The $V_2O_4$ used in the present invention can be prepared by reducing $V_2O_5$ by using an appropriate method such as, for example, reducing $V_2O_5$ in a hydrogen stream in a vapor phase at high temperatures, or reducing $V_2O_5$ suspended in an aqueous solution with a reducing agent such as hydroxylamine, hydrazine, oxalic acid, formic acid and the like. A further example may be the method comprising suspending $V_2O_5$ in isobutyl alcohol, a mixture of isobutyl alcohol and benzyl alcohol, or the like and heating with stirring or refluxing to reduce $V_2O_5$ in an organic solvent.

As are shown in the Description of the Related Art, various methods of using a polyhydric alcohol as an organic solvent for reducing $V_2O_5$ in an organic solvent are already described. According to these methods, a large amount of polyhydric alcohol is used so that the reaction mixture becomes highly viscous and stirring of the solvents and the mixed slurry is difficult, or the polyhydric alcohol is oxidized by $V_2O_5$ to form a diketone, ketoaldehyde or the like, and condensation products as by-products having high boiling points are accumulated in the solvent and disturb the treatment for recycling the solvent.

According to the method for producing a catalyst precursor, $(VO)_2H_4P_2O_9$ by adding a polyhydric alcohol to a solvent upon reducing $V_2O_5$ and reacting the resulting $V_2O_4$ with phosphoric acid, the above-mentioned high boiling point by products are present together with the desired precursor so that a portion of the slurry of the precursor is solidified and a uniform slurry can not be obtained. In the case where a solidified precursor precipitates upon the precursor forming reaction whereby stirring can not be uniformly conducted, the yield of the precursor is lowered and, the property of the catalyst, i.e. the end product, becomes non-uniform and the yield of maleic anhydride by the oxidation of butane is low.

In a system where a polyol coexists with a solvent from the $V_2O_5$ reduction step, lump-like agglomerations having particle sizes as large as several cm. are formed in the later step where a reaction with phosphoric acid is effected, and $V_2O_4$ confined inside the agglomeration can not react with phosphoric acid so that the $V_2O_4$ remains unreacted. $V_2O_4$ having reacted with phosphoric acid becomes a catalyst precursor of the formula $(VO)_2H_4P_2O_9$. However, since some unreacted $V_2O_4$ is present in the lumps, the resulting catalyst becomes non-uniform as a whole, that is, the finally produced catalyst component is a mixture of $(VO)_2P_2O_7$ and a small amount of $V_2O_4$. When the unreacted $V_2O_4$ is used as a catalyst for oxidizing butane, maleic anhydride is scarcely formed, but carbon monoxide and carbon dioxide are formed and thereby the yield of maleic anhydride is lowered per unit amount of the catalyst.

In a system where a diol coexists from the reducing step, the remaining amount of unreacted $V_2O_4$ confined in the lumps amount to several to 10 wt %.

According to the process of the present invention where a polyol coexists only at the step of the reaction of phosphoric acid with $V_2O_4$, lump-like agglomerations are not formed in the reaction slurry, but a uniform slurry is formed and unreacted $V_2O_4$ scarcely remains. As a result, a uniform $(VO)_2P_2O_7$ can be produced.

According to the present invention, the reaction of $V_2O_4$, which has been already produced by reduction in a solvent, with phosphoric acid is carried out in an organic solvent in the presence of a polyol, and there are not produced a diketone, ketoaldehyde or the like in the solvent and there is not any problem which has occurred with respect to materials used in the conventional methods. Therefore, there can be obtained a uniform slurry of the catalyst precursor.

In view of the foregoing, the yield of the catalyst precursor is high and the performance and property of the subsequently produced catalyst are also always uniform and the reproducibility thereof is very good. The yield of maleic anhydride by oxidizing butane in the presence of the said catalyst is better than that by using conventional catalysts. According to the process of the present invention, the polyol is not used as a solvent, but as an additive so that the amount of polyol is less than that in conventional method and can give a sufficient and satisfactory effect.

The organic solvent used for the reaction of $V_2O_4$ with phosphoric acid includes isobutyl alcohol, a mixture of isobutyl alcohol and benzyl alcohol and the like. The boiling point of the organic solvent is usually 100° C. or higher, preferably 100°–200° C.

The additive used in the reaction of $V_2O_4$ with phosphoric acid is a polyol. When a primary, secondary or tertiary monoalcohol is used as the additive, no effect is recognized. When an aminoalcohol, diamine, diketone, ketoalcohol or the like is used, the reaction of $V_2O_4$ with phosphoric acid is hindered so that such compounds are not suitable as the additive.

Polyols as additives include ethylene glycol, propanediol, butanediol, diethylene glycol, triethylene glycol, glycerol, glucose, gluconic acid and the like. The amount of polyol is preferably 0.5–3 moles per mole of $V_2O_4$.

The specific surface area of the catalyst can be controlled to a certain range by selecting the type of polyol. Similarly the degree of crystallinity of the resulting catalyst can be changed by selecting the type of polyol. For example, when a diol is added, the specific surface area increases and the degree of crystallinity is decreased. The addition results in the formation of a catalyst which is nearer to the amorphous form as compared with no diol being added. Therefore, the layer-like structure of the catalyst, $(VO)_2P_2O_7$, is disturbed and the attrition loss thereof is lowered when used as a fluidized bed catalyst.

Examples of suitable phosphoric acids include orthophosphoric acid, metaphosphoric acid and pyrophosphoric acid and mixtures thereof. The atomic ratio of vanadium to phosphorus (V/P ratio) to be reacted is preferably in the range of from 0.9 to 1.5.

In the process of the invention, it is preferable to carry out the reaction with heating under reflux at atmospheric pressure. The water formed by the reaction separated such as by the azeotropic distillation. It is also possible to carry out the reaction at an elevated temperature at an increased pressure. The reaction requires a period of time of from several hours to about 20 hours.

With the progress of the reaction between vanadium oxide and phosphoric acid, blue to bluish green precipitates of the catalyst precursor consisting mainly of $(VO)_2H_4P_2O_9$ are generated in the solvent. After completion of the reaction, the catalyst precursor is separated from the solvent e.g. by filtration. After being separated, the catalyst precursor is washed with a solvent such as isopropyl alcohol, acetone or the like. Thereafter, it is suspended in water and well stirred to form a uniform slurry. The solid concentration of the slurry is preferably in the range of from 20 to 50 % by weight, and the viscosity of the slurry is preferably in the range of 10 to 500 cp. The thus-obtained slurry is spray-dried to form microspheres suitable as a catalyst to be used in fluidized beds. The microspheres preferably have an average particle size of 40 to 80 $\mu$m, and the particle size of the microspheres is distributed preferably over a wide range such as a range of 20–150 $\mu$m. The strength, in particular, attrition-resistance of the catalyst can be improved by appropriately adding a second component such as silica sol or the like with the catalyst precursor in an aqueous slurry that is spray-dried.

The microspheres of the catalyst precursor can be calcined at a temperature of 400° to 600° C. in a stream of an inert gas such as nitrogen or the like, a mixture of nitrogen and air, or a mixture of butane and air, to produce the catalyst. The calcination is preferably carried out in a fluidized bed.

The starting material for maleic anhydride is butane. The butane may be composed of n-butane alone, but may contain additionally small amounts of isobutane, butenes, propane, pentanes and the like.

Oxidation of the butane is usually carried out at 300°–450° C. In accordance with the process of the present invention, there can be obtained a catalyst having a high density and highly attrition-resistance which exhibits excellent catalyst activity at lower temperatures. When the catalyst according to the invention is used in a reactor utilizing a fluidized bed, the reactor ca be operated stably for a prolonged period of time since the catalyst has a long life-time due to its increased mechanical strength and decreased attrition loss. At the same time, the amount of additional catalyst to be charged can be reduced, and the yield of maleic anhydride can be improved.

catalyst precursor was prepared without using any polyols. In Examples 2 to 5, various polyols indicated in Table 1 were employed. The results are shown in Table 1.

TABLE 1

| Maleic Anhydride | Polyol | Charged Bulk Density (g/ml) | Attrition Loss (%/hr) | Reaction Temperature (°C.) | Yield of Maleic Anhydride (mol %) | Specific Surface Area (m²/g) | Remaining $V_2O_4$ (wt %) |
| --- | --- | --- | --- | --- | --- | --- | --- |
| Comparative Example 1 | None | 0.65 | 1.85 | 430 | 53 | 23 | 0.1 |
| Example 2 | Ethylene glycol | 1.12 | 0.62 | 385 | 60 | 30 | 0.3 |
| Example 3 | Diethylene glycol | 1.09 | 0.65 | 390 | 59 | 54 | 0.2 |
| Example 4 | Gluconic acid | 1.06 | 0.75 | 390 | 58 | 42 | 0.3 |
| Example 5 | Glycerol | 1.07 | 0.64 | 380 | 60 | 45 | 0.2 |

Remaining $V_2O_4$: Unreacted $V_2O_4$ remaining in the catalyst before calcination.

The present invention will be explained further in detail referring to the following examples and comparative examples.

EXAMPLE 1

A total of 20 kg of powdered $V_2O_5$ was gradually added with stirring to a mixture of alcohols (150 liters) consisting of 65% by volume of isobutyl alcohol and 35% by volume of benzyl alcohol. The resulting mixture was heated under reflux with stirring for 2 hours to reduce $V_2O_5$ to $V_2O_4$ while water was removed by azeotropic distillation. The resulting alcohol solution of $V_2O_4$ was cooled to 40° to 50° C., and 20 kg of 1,4-butanediol was added thereto with stirring. Subsequently, 25 kg of 85% orthophosphoric acid was added dropwise to the mixture with stirring. The resulting mixture was heated under reflux with thorough stirring for a period of 2 hours, while separating water as an azeotrope from the reaction system. After the reaction mixture was cooled to room temperature, the catalyst precursor was collected by filtration and washed with isopropyl alcohol. The thus-obtained catalyst precursor was pulverized, suspended in water and thoroughly mixed with a homogenizing mixer to give a slurry having a solid content of 40 wt %.

The slurry was shaped into microspheres by using a spray drier of the pressurized-nozzle type. The thus-obtained microspheres were calcined in a fluidized bed at 500° C. for 4 hours in a stream of a mixture of nitrogen and air (4:1) to give the desired catalyst. The thus-obtained catalyst had a specific surface area of 40 m²/g, an average particle size of 50 μm, and a particle size distribution of from 15 to 120 μm. The catalyst had a charged bulk density (C.B.D.) of 1.1 g/ml and gave an attrition loss of 0.57%/hr when determined in accordance with the ACC method [the standardized method (accelerated test) for determining the attrition loss of fluidization catalyst].

Maleic anhydride was produced by oxidizing n-butane in a fluidized bed, using the catalyst prepared above. Air containing 3.2% by volume of n-butane was introduced into the reactor at a space velocity of 500 hr$^{-1}$. The temperature of the catalyst layer was 380° C. There was obtained maleic anhydride at a yield of 60 mole %, based on butane introduced thereinto.

COMPARATIVE EXAMPLE 1 AND EXAMPLES 2-5

Catalysts were prepared and tested in a similar manner as in Example 1. In Comparative Example 1, the

COMPARATIVE EXAMPLE 2

A total of 2 kg of powdered of $V_2O_5$ was gradually added with stirring to a mixture of alcohols (15 liters) consisting of 30% by volume of isobutyl alcohol, 20% by volume of benzyl alcohol and 50% by volume of ethylene glycol. The resulting mixture was heated under reflux with stirring for 2.5 hours while removing water as an azeotrope to reduce $V_2O_5$ to $V_2O_4$.

The resulting alcohol solution of $V_2O_4$ was cooled to 40° C., and 2.5 kg of 85% orthophosphoric acid was added dropwise thereto with stirring. The resulting mixture was refluxed with stirring for 2.5 hours while separating water as an azeotrope from the reaction system. While adding the phosphoric acid dropwise, precipitates were formed and thereby the stirring could not be uniformly effected and the resulting catalyst precursor was not in the form of a uniform slurry. The slurry portion was blue while the solid portion was green. The non-uniform precipitate was ground, filtered and washed with isopropyl alcohol. 5.1 wt % of unreacted $V_2O_4$ was contained in the resulting precipitate. After the washing, the catalyst precursor was ground, suspended in water, mixed with a homomixer to obtain a slurry having a concentration of solid of 39% by weight.

The resulting slurry was made into microspheres by using a spray drier of the pressurized-nozzle type. The resulting microspheres were calcined under fluidization at 500° C. for 4 hours in a stream of a mixture of nitrogen and air (4:1) to produce the catalyst. The resulting catalyst had a specific surface area of 27 m²/g, an average particle size of 48 μm and a particle size distribution of from 15 to 120 μm. The catalyst had a charged bulk density of 0.80 g/ml and an attrition loss measured by the ACC method of 1.3%/hr. The thus-obtained catalyst was used for butane oxidation reaction following the procedure of Example 1. At a catalyst bed temperature of 400° C., the yield of maleic anhydride was 54%.

We claim:

1. A process for producing a catalyst precursor for oxidizing butane to maleic anhydride which comprises reacting $V_2O_4$ with phosphoric acid in an atomic ratio of vanadium to phosphorus of from 0.9 to 1.5 in an organic solvent in the presence of a polyol.

2. The process according to claim 1 wherein the organic solvent has a boiling point of 110° to 200° C.

3. The process according to claim 1 wherein the organic solvent is selected from the group consisting of isobutyl alcohol and a mixture of isobutyl alcohol and benzyl alcohol.

4. The process according to claim 1 wherein the polyol is selected from the group consisting of ethylene glycol, propanediol, butanediol, diethylene glycol, triethylene glycol, glycerol, glucose and gluconic acid.

5. A catalyst for producing maleic anhydride by oxidizing butane prepared from the catalyst precursor of claim 1.

* * * * *